(12) United States Patent
Carrison et al.

(10) Patent No.: US 8,118,829 B2
(45) Date of Patent: Feb. 21, 2012

(54) CLOT REMOVAL DEVICE

(75) Inventors: Harold F. Carrison, Pleasanton, CA (US); Roger Farnholtz, Fremont, CA (US)

(73) Assignees: Stryker Corporation, Kalamazoo, MI (US); Stryker NV Operations Limited, Dublin (IE)

( * ) Notice: Subject to any disclaimer, the term of this patent is extended or adjusted under 35 U.S.C. 154(b) by 1064 days.

(21) Appl. No.: 12/019,235

(22) Filed: Jan. 24, 2008

(65) Prior Publication Data

US 2008/0114393 A1    May 15, 2008

Related U.S. Application Data

(63) Continuation of application No. 10/689,893, filed on Oct. 21, 2003, now Pat. No. 7,344,550.

(51) Int. Cl.
*A61M 29/00* (2006.01)
(52) U.S. Cl. ........................................ 606/200
(58) Field of Classification Search .................. 606/113, 606/114, 127, 159, 200
See application file for complete search history.

(56) References Cited

U.S. PATENT DOCUMENTS

| | | |
|---|---|---|
| 4,046,150 A | 9/1977 | Schwartz et al. |
| 4,198,960 A | 4/1980 | Utsugi |
| 4,347,846 A | 9/1982 | Dormia |
| 4,873,978 A | 10/1989 | Ginsburg |
| 4,998,539 A | 3/1991 | Delsanti |
| 5,171,233 A | 12/1992 | Amplatz et al. |
| 5,192,286 A | 3/1993 | Phan et al. |
| 5,330,482 A | 7/1994 | Gibbs et al. |
| 5,486,183 A | 1/1996 | Middleman et al. |
| 5,496,330 A | 3/1996 | Bates et al. |
| 5,527,326 A | 6/1996 | Hermann et al. |
| 5,662,671 A | 9/1997 | Barbut et al. |
| 5,720,754 A | 2/1998 | Middleman et al. |
| 5,772,609 A | 6/1998 | Nguyen et al. |
| 5,820,628 A | 10/1998 | Middleman et al. |
| 5,895,398 A | 4/1999 | Wensel et al. |
| 5,904,690 A | 5/1999 | Middleman et al. |
| 5,980,554 A | 11/1999 | Lenker et al. |
| 6,053,932 A | 4/2000 | Daniel et al. |
| 6,066,158 A | 5/2000 | Engelson et al. |
| 6,139,510 A | 10/2000 | Palermo |
| 6,146,396 A | 11/2000 | Konya et al. |
| 6,152,946 A * | 11/2000 | Broome et al. ............... 606/200 |
| 6,168,603 B1 | 1/2001 | Leslie et al. |
| 6,183,495 B1 | 2/2001 | Lenker et al. |
| 6,346,116 B1 * | 2/2002 | Brooks et al. ............... 606/200 |
| 6,350,271 B1 | 2/2002 | Kurz et al. |
| 6,391,044 B1 * | 5/2002 | Yadav et al. ............... 606/200 |
| 6,402,771 B1 | 6/2002 | Palmer et al. |
| 6,458,139 B1 | 10/2002 | Palmer et al. |

(Continued)

FOREIGN PATENT DOCUMENTS

EP    0472368 A    2/1992

*Primary Examiner* — Kevin T Truong
(74) *Attorney, Agent, or Firm* — Vista IP Law Group LLP

(57) ABSTRACT

A device for removing blood clots and methods of making and using the same. The clot pulling device may include a shaft and one or more strut members that each may include a loop region. The proximal ends of the strut members may be attached to the shaft and the distal ends of the strut members may be coupled to the shaft.

20 Claims, 5 Drawing Sheets

U.S. PATENT DOCUMENTS

| | | |
|---|---|---|
| 6,468,291 B2 | 10/2002 | Bates et al. |
| 6,592,607 B1 | 7/2003 | Palmer et al. |
| 6,638,294 B1 | 10/2003 | Palmer |
| 2002/0143361 A1 | 10/2002 | Douk et al. |
| 2003/0078605 A1 | 4/2003 | Bashiri et al. |
| 2003/0153944 A1 | 8/2003 | Phung et al. |

* cited by examiner

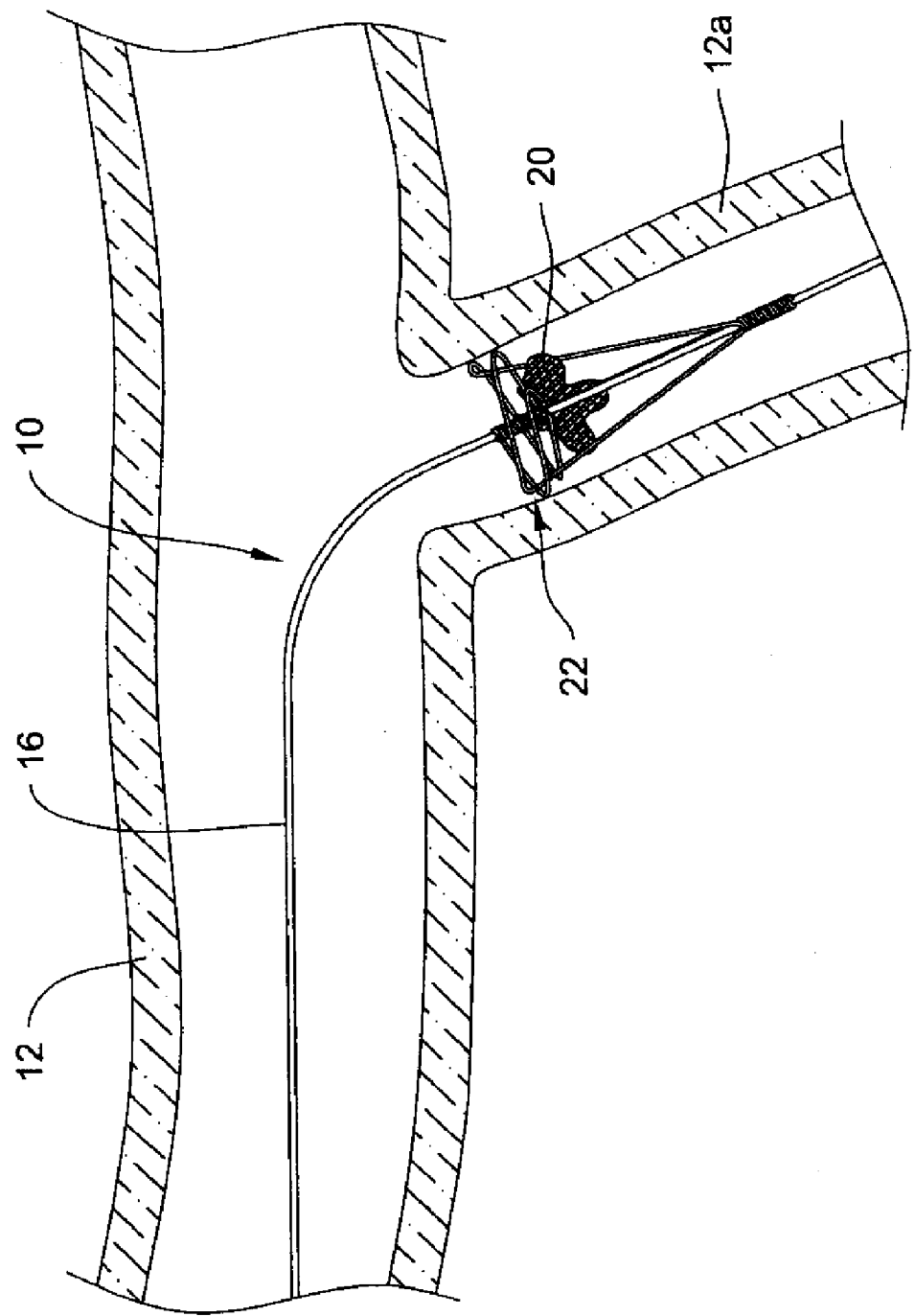

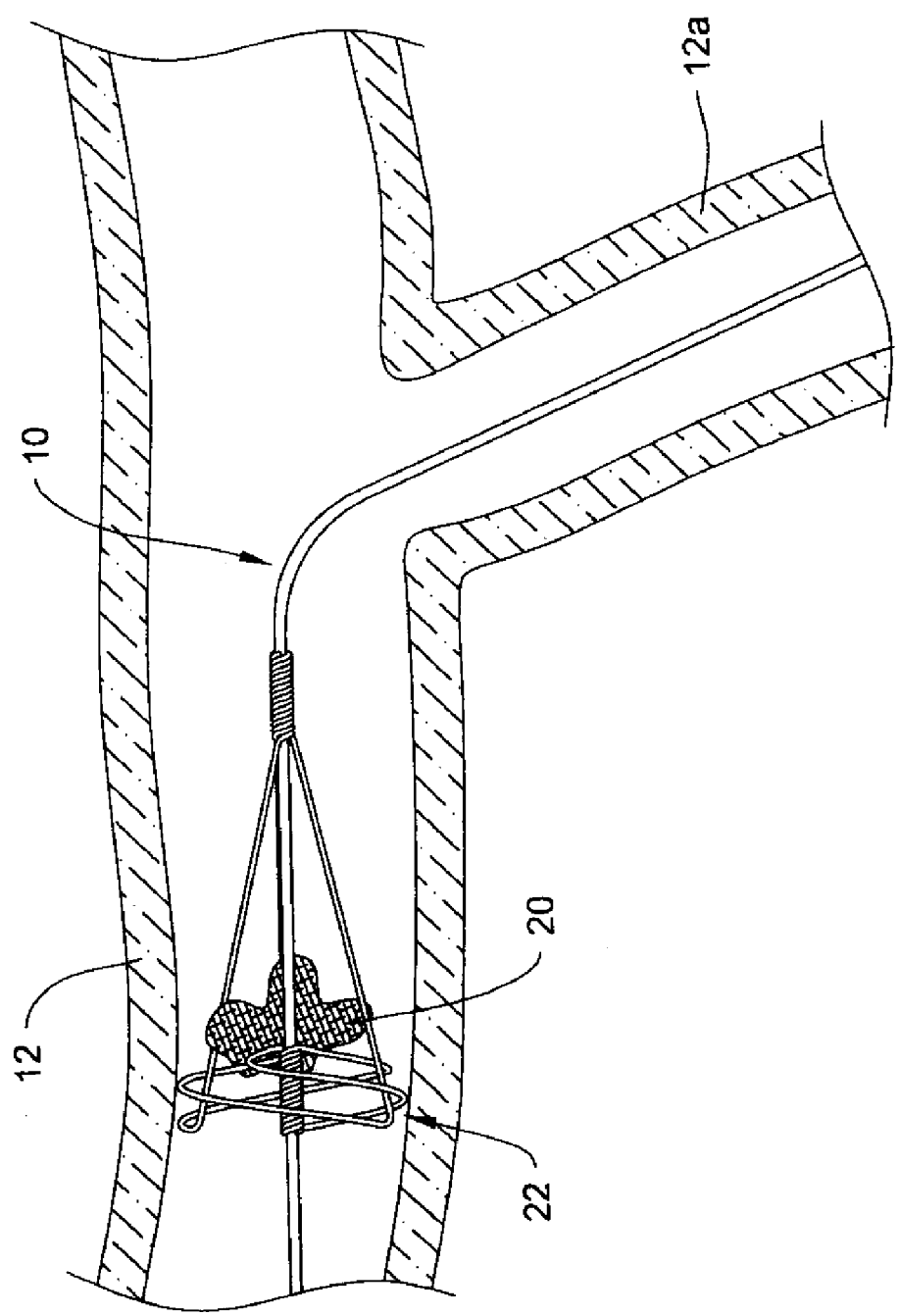

CLOT REMOVAL DEVICE

RELATED APPLICATIONS

This application is a continuation of U.S. application Ser. No. 10/689,893, filed Oct. 21, 2003.

FIELD OF THE INVENTION

The present invention pertains to intravascular medical devices. More particularly, the present invention pertains to devices for capturing and removing blood clots from a blood vessel.

BACKGROUND

The present invention pertains generally to emboli collection and removal.

Blood thrombus, may form a clot in a patient vasculature. Sometimes such clots are harmlessly dissolved in the blood stream. At other times, however, such clots may lodge in a blood vessel where they can partially or completely occlude the flow of blood. If the partially or completely occluded vessel feeds blood to sensitive tissue such as, the brain, lungs or heart, for example, serious tissue damage may result.

When symptoms of an occlusion are apparent, such as an occlusion resulting in a stroke, immediate action should be taken to reduce or eliminate resultant tissue damage. One approach is to treat a patient with clot dissolving drugs. These drugs, however, do not immediately dissolve the clot from the patient.

BRIEF SUMMARY

The present invention pertains to devices for removing blood clots from blood vessels. In at least some embodiments, a clot removal device includes a shaft and one or more strut members. Each of the one or more strut members may include a proximal end that is attached to the shaft, a loop region, and a distal end that is coupled to the shaft. These and some of the other structural features and characteristics are described in more detail below.

BRIEF DESCRIPTION OF THE DRAWINGS

FIG. 4 is a partial cross-sectional plan view of an example medical device disposed within a blood vessel; and FIG. 5 is a another partial cross-sectional plan view of an example medical device disposed within a blood vessel where the device has transitioned between differing blood vessels or vascular regions.

DETAILED DESCRIPTION

Figure 1:
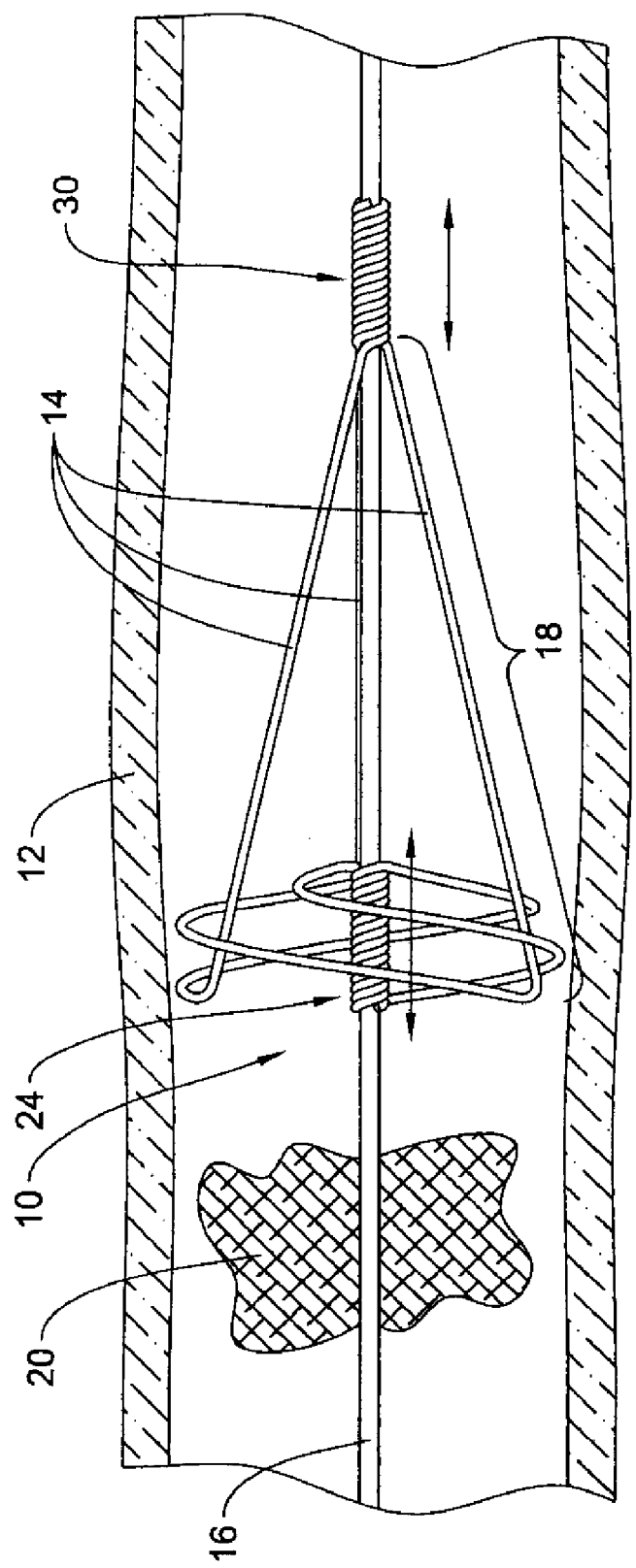
FIG. 1 is a partial cross-sectional side view of an example medical device.

The following description should be read with reference to the drawings wherein like reference numerals indicate like elements throughout the several views. The detailed description and drawings illustrate example embodiments of the claimed invention.

For a number of reasons, it may be desirable to capture and/or remove clots from the vasculature. FIG. 1 is a partial cross-sectional side view of an example clot pulling medical device 10 disposed in a blood vessel 12. Blood vessel 12 can be essentially any vessel. Device 10 may include a plurality of struts 14 coupled to an elongate shaft or guidewire 16. Struts 14 may define a basket member or region 18, suitable for capturing a blood clot 20 disposed in the vasculature. In general, device 10 can be advanced through the vasculature to a suitable location, for example adjacent clot 20, and configured so that clot 20 can be captured in basket region 18. Device 10 and the captured clot 20 can be removed from the vasculature.

In at least some embodiments, struts 14 may include a proximal end region 24 and a distal end region 30. End regions 24/30 generally define the position where struts 14 and shaft 16 are coupled to one another. The form or configuration of this coupling may vary. For example, end regions 24/30 may be wound or coiled about shaft 16. Alternatively, end regions 24/30 may be coupled to shaft by a mechanical connection or connector, thermal bond, weld, adhesive bond, and the like, or combinations thereof. In some embodiments, end regions 24/30 are fixedly attached to shaft 16. For example, end regions 24/30 may be wound so that a mechanical bond is formed between shaft 16 and struts 14. Alternatively, end regions 24/30 may be fixedly attached via the other coupling means described above or in any other suitable way.

Instead of being fixedly attached, proximal end region 24, distal end region 30, or both end regions 24/30 may be slidable along shaft 16. For example, either end region 24 or end region 30 can be slidable along shaft 16 with the non-slidable end region being fixedly attached. Alternatively, both end regions 24/30 can be slidably coupled to shaft 16. The manner in which end regions 24/30 are slidably coupled to shaft 16 may vary. For example, end region 24/30 may be coiled about shaft 16 in a manner that allows the coiled end regions 24/30 to slide or move along shaft 16. Alternatively, end regions 24/30 may be attached to a tubular structure or member that is slidably disposed along shaft 16. Slidability is illustrated in FIG. 1 by double-headed arrows located below end regions 24/30, which indicate that end regions 24/30 may be movable in either the proximal or distal direction. Slidability may be desirable, for example, by allowing one or both of end regions 24/30 to be moved in order to collapse or expand device 10. For example, proximal end region 24 can be moved in the proximal direction, distal end region 30 can be moved in the distal direction, or both end regions 24/30 can be moved in these directions so that device 10 (i.e., basket region 18) collapses. Collapsing may be desirable, for example, by reducing the profile of device 10 so as to improve transportation (e.g., delivery and/or retrieval) of device 10 through the vasculature.

Figure 2:
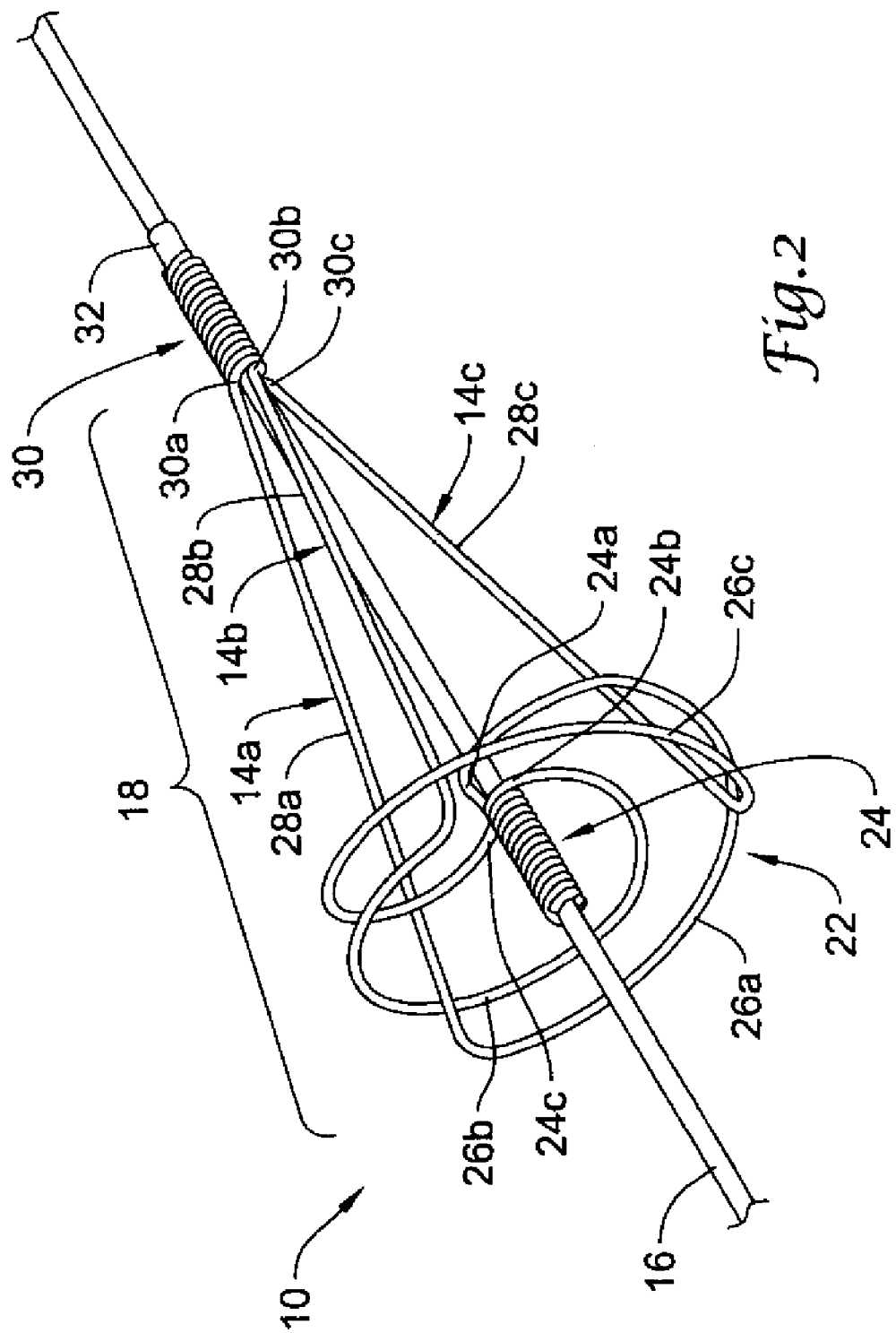
FIG. 2 is a perspective view of an example medical device.

Turning now to FIG. 2, it can be seen that struts 14 (which are individually indicated in FIG. 2 as struts 14a, 14b, and 14c) may define a mouth or opening 22 of basket region 18. For example, struts 14 may include a number of bends or curves so mouth 22 may be "petal shaped" or otherwise extend around shaft 16 in a manner that defines a petal-shaped opening 22. According to this embodiment, each strut 14a/b/c may include a proximal end 24a/b/c coupled to shaft 16 and disposed adjacent end region 24, an arched or looped region 26a/b/c adjacent proximal end 24a/b/c, a distally-extending strut region 28a/b/c, and a distal end 30a/b/c coupled to shaft 16 and disposed adjacent end region 30. Additionally, struts 14a/b/c may be connected or coupled with one another (at one or more connection points) in a folded sheet configuration or construction. Proximal ends 24a/b/c may be attached to shaft 16 in a number of different manners. For example, proximal ends 24a/b/c may be wound about shaft 16, mechanical bonded (e.g., by crimping, attached by placing a sleeve over ends 24a/b/c, etc.), thermally bonding, welding, brazing, adhesively bonding, or in any other suitable manner. In some embodiments, proximal ends 24a/b/c are directly attached to shaft 16 while in other embodiments, proximal ends 24a/b/c may be attached to another structure that is disposed over or otherwise coupled to shaft 16. For example, ends 24a/b/c may be coupled to a tube or tubular sleeve coupled to shaft 16. As described above, ends 24a/b/c (and/or end region 24) may be fixedly attached to shaft 16 or slidable over shaft 16.

Looped regions 26a/b/c may generally loop circumferentially about a portion of shaft 16. The extent that each looped region 26a/b/c loops about shaft 16 may vary depending on the number of struts included. For example, FIG. 2 illustrates that mouth 22 and/or basket region 18 can include three struts 14a/b/c. However, this number of struts is only illustrative in nature as any suitable number (e.g., 1, 2, 3, 4, 5, 6, or more) of struts may used. Thus, by including three struts 14a/b/c, it may be desirable for each looped region 26a/b/c to extend around about one-third or more (i.e., about 120 degrees or more) of the circumferential area around shaft 16.

In addition, it may be desirable for adjacent looped regions 26a/b/c to overlap. For example, overlapping looped regions 26a/b/c or allowing these regions to overlap may allow mouth 22 to be adapted to appose blood vessels of differing sizes. This characteristic is described in more detail below. It can be appreciated that overlapping looped regions 26a/b/c may also vary the amount of circumferential area that each looped region 26a/b/c extends around shaft 16. For example, it may be desirable to overlap adjacent looped regions 26a/b/c in the range of about 5 percent to about 30 percent, or more. Accordingly, looped regions 26a/b/c may extend about 120 degrees (no overlap) or about 126 degrees (5 percent overlap) to about 156 degrees (30 percent overlap), or more. The amount of circumferential area that each looped region 26a/b/c need not be the same as each may span differing portions and overlap to differing degrees.

In some embodiments, particularly those where looped regions 26a/b/c overlap, it may be desirable for looped regions 26a/b/c to be somewhat angled so that adjacent loops 26a/b/c do not interfere with one another. For example, one end of looped regions 26a/b/c (e.g., the end closer to proximal ends 24a/b/c) may be further away from shaft 16 than another end of looped regions 26a/b/c (e.g., the end closer to distally-extending regions 28a/b/c). Accordingly, looped regions 26a/b/c can freely overlap without adjacent looped regions 26a/b/c distorting or displacing one another. Alternatively, the mere fact that looped regions 26a/b/c are curved may allow sufficient space adjacent overlapped regions. In still other alternative embodiments, it may be desirable or acceptable for adjacent, overlapping looped regions 26a/b/c to contact one another.

Looped regions 26a/b/c may be formed in a number of different ways. For example, looped regions 26a/b/c may be formed by disposed a shaft about a mandrel or other suitable molding device. In embodiments where struts 14a/b/c are comprised of a shape-memory material, the molded or bended shaft may be heat treated to set the desired shape, corresponding to looped regions 26a/b/c, within the material. It can be appreciated that any of the other portions of struts 14a/b/c may be analogously worked so as to have the desired shape, characteristics, and features.

Distally-extending regions 28a/b/c generally extend from looped regions 26a/b/c toward distal ends 30a/b/c. Regions 28a/b/c generally extend along shaft 16. In some embodiments, regions 28a/b/c extend generally parallel to shaft 16 while in other embodiments, regions 28a/b/c may converge inward toward shaft 16. The length of regions 28a/b/c may vary depending on the desired configuration of device 10 and/or basket region 18. It can be appreciated that as the length of regions 28a/b/c increases, the area of basket region 18 increases. It may be desirable to use devices 10 with generally increased basket 18 area to capture relatively large clots or when used in relatively large vessel. Conversely, it may be desirable to use devices 10 with generally decreased area in sensitive or small vascular areas.

Distal ends 30a/b/c may be attached to shaft 16 in a manner similar to how proximal ends 24a/b/c are attached. For example, distal ends 30a/b/c may be wound about shaft 16. In some embodiments, distal ends 30a/b/c may be fixedly attached to shaft 16 while in others the windings of distal ends 30a/b/c may be slidable or otherwise moveable along shaft 16. This later embodiment may be desirable, for example, by allowing device 10 and/or basket region 18 to be collapsed by pulling or shifting the position of distal ends 30a/b/c in the distal direction. Accordingly, basket 18 can be collapsed and, for example, be disposed in a delivery sheath. Proximally retracting the sheath relative to device 10 may allow distal ends 30a/b/c to shift or move proximally and expand basket 18. In some embodiments, the slidability of distal ends 30a/b/c may be enhanced by coupling ends 30a/b/c to a tubular member 32 slidably disposed over shaft. Tube 32 may comprise a hypodermic tube (i.e., a "hypotube"), metal or polymer sleeve, or any other suitable structure. Although tube 32 is shown with respect to distal ends 30a/b/c and distal end region 30, the use of tube 32 at proximal end region 24 is contemplated and may be used in some embodiments of device 10.

The manufacturing of device 10 may generally include forming struts 14a/b/c into the desired shape and coupling them to shaft 16. In some embodiments, forming struts 14a/b/c may include disposing a shaft material on a mandrel or otherwise working the material so as to define the various regions of struts 14a/b/c. Coupling struts 14a/b/c to shaft 16 may include winding proximal ends 24a/b/c and/or distal ends 30a/b/c about shaft 16. In addition or in the alternative, distal ends 30a/b/c may be attached to tubular member 32 as described above. It should also be noted that although shaft 16 is described above as being a guidewire, shaft 16 should not be interpreted to being limited to being just a guidewire. It can be appreciated that shaft 16 could be any intravascular device or be any device designed to pass through an opening or body lumen. For example, the device may comprise a catheter (e.g., therapeutic, diagnostic, or guide catheter), endoscopic device, laproscopic device, or any other suitable device. Additionally, in embodiments where shaft 16 is a structure other than a guidewire, the steps of attaching struts 14a/b/c can be varied slightly in order accommodate the differing sizes and shapes of these structures.

In some other embodiments, device 10 may be manufactured by laser-cutting, laser etching, chemical etching, or photo-chemical etching a tubular structure so as to define struts 14a/b/c and basket 18. For example, basket 18 and struts 14a/b/c can be defined by laser-cutting a tubular structure such as a hypodermic tube (i.e., a "hypotube"). This manufacturing method may be desirable for a number of reasons. For example, this method may allow struts 14a/b/c and basket 18 to be formed in a relatively simple manner, with relatively few manufacturing steps. Additionally, following this method may allow shaft 16 to be defined by the proximal region of the hypotube. Accordingly, the manufacturing method may be further simplified by not requiring any welding or attaching steps to connect various structures of device 10. Alternatively, device 10 may be manufactured by cutting or forming the appropriate structures into a generally planar sheet of material and then, if necessary, attaching the ends of the planar structure or attaching one or more planar structures together in any suitable manner. For example, the opposing sides of a sheet of material may be attached, welded, adhesively bonded, bonded with a polymer strip, thermally bonded, a mechanically connected, and the like, or in any other suitable manner.

All or portions of device 10 may be manufactured from any suitable material including metals, metal alloys, polymers, etc. Some examples of suitable metals and metal alloys include stainless steel, such as 304V, 304L, and 316L stainless steel; linear-elastic or super-elastic nitinol or other nickel-titanium alloys, nickel-chromium alloy, nickel-chromium-iron alloy, cobalt alloy, tungsten or tungsten alloys, MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si), hastelloy, monel 400, inconel 825, or the like; or other suitable material.

Some examples of suitable polymers may include polytetrafluoroethylene (PTFE), ethylene tetrafluoroethylene (ETFE), fluorinated ethylene propylene (FEP), polyoxymethylene (POM), polybutylene terephthalate (PBT), polyether block ester, polyurethane, polypropylene (PP), polyvinylchloride (PVC), polyether-ester (for example a polyether-ester elastomer such as ARNITEL® available from DSM Engineering Plastics), polyester (for example a polyester elastomer such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), silicones, polyethylene (PE), Marlex high-density polyethylene, Marlex low-density polyethylene, linear low density polyethylene (for example REXELL®), polyethylene terephthalate (PET), polyetheretherketone (PEEK), polyimide (PI), polyetherimide (PEI), polyphenylene sulfide (PPS), polyphenylene oxide (PPO), polysulfone, nylon, perfluoro(propyl vinyl ether) (PFA), other suitable materials, or mixtures, combinations, copolymers thereof, polymer/metal composites, and the like. In some embodiments portions or all of device 10 can be blended with a liquid crystal polymer (LCP). For example, the mixture can contain up to about 5% LCP.

In some embodiments, a coating, for example a lubricious, a hydrophilic, a protective, or other type of coating may be applied over portions of or all of device 10. Hydrophobic coatings such as fluoropolymers provide a dry lubricity which improves device exchanges. Lubricious coatings improve steerability and improve lesion crossing capability. Suitable lubricious polymers are well known in the art and may include silicone and the like, hydrophilic polymers such as polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference. In some embodiments, the sheath or coating may be applied over basket region 18. This may provide extra surface area to contain clots that might be captured therein.

The sheath or polymeric layer coating may be formed, for example, by coating, by extrusion, co-extrusion, interrupted layer co-extrusion (ILC), or fusing several segments end-to-end. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

Device 10, or portions thereof, may also be coated, plated, wrapped or surrounded by, doped with, or otherwise include a radiopaque material. For example, struts 14a/b/c may be made from a radiopaque material or may include a radiopaque marker member or coil coupled thereto. Radiopaque materials are understood to be materials capable of producing a relatively bright image on a fluoroscopy screen or another imaging technique during a medical procedure. This relatively bright image aids the user of device 10 in determining its location. Some examples of radiopaque materials can include, but are not limited to, gold, platinum, palladium, tantalum, tungsten alloy, plastic material loaded with a radiopaque filler, and the like.

In some embodiments, a degree of MRI compatibility may be imparted into device 10. For example, to enhance compatibility with Magnetic Resonance Imaging (MRI) machines, it may be desirable to make portions of device 10, in a manner that would impart a degree of MRI compatibility. For example, device 10, or portions thereof, may be made of a material that does not substantially distort the image and create substantial artifacts (artifacts are gaps in the image). Certain ferromagnetic materials, for example, may not be suitable because they may create artifacts in an MRI image. Device 10, or portions thereof, may also be made from a material that the MRI machine can image. Some materials that exhibit these characteristics include, for example, tungsten, Elgiloy, MP35N, nitinol, and the like, and others.

As stated above, device 10 and/or basket region 18 may be configured to shift between a first generally collapsed configuration and a second generally expanded configuration. In at least some embodiments, shifting between these configurations includes the longitudinal movement of distal ends 30a/b/c as described above. In some embodiments, device 10 or portions thereof may be made of a shape-memory material (such as nickel-titanium alloy) that can assume a pre-defined shape when unconstrained or when subjected to particular thermal conditions. According to this embodiment, device 10 can be manufactured to be "self-expanding" so that it can be delivered in a collapsed configuration (i.e., with distal ends 30a/b/c pulled or moved distally to collapse basket 18) then shift to the expanded configuration when a constraint (e.g., a delivery sheath) is removed or when device 10 is subject to the thermal conditions within blood vessel 12. This feature could also be used at proximal ends 24a/b/c. Alternatively, shifting may occur by mechanically moving proximal ends 24a/b/c or distal ends 30a/b/c, for example, by an attached or separately provided shaft.

Figure 3:
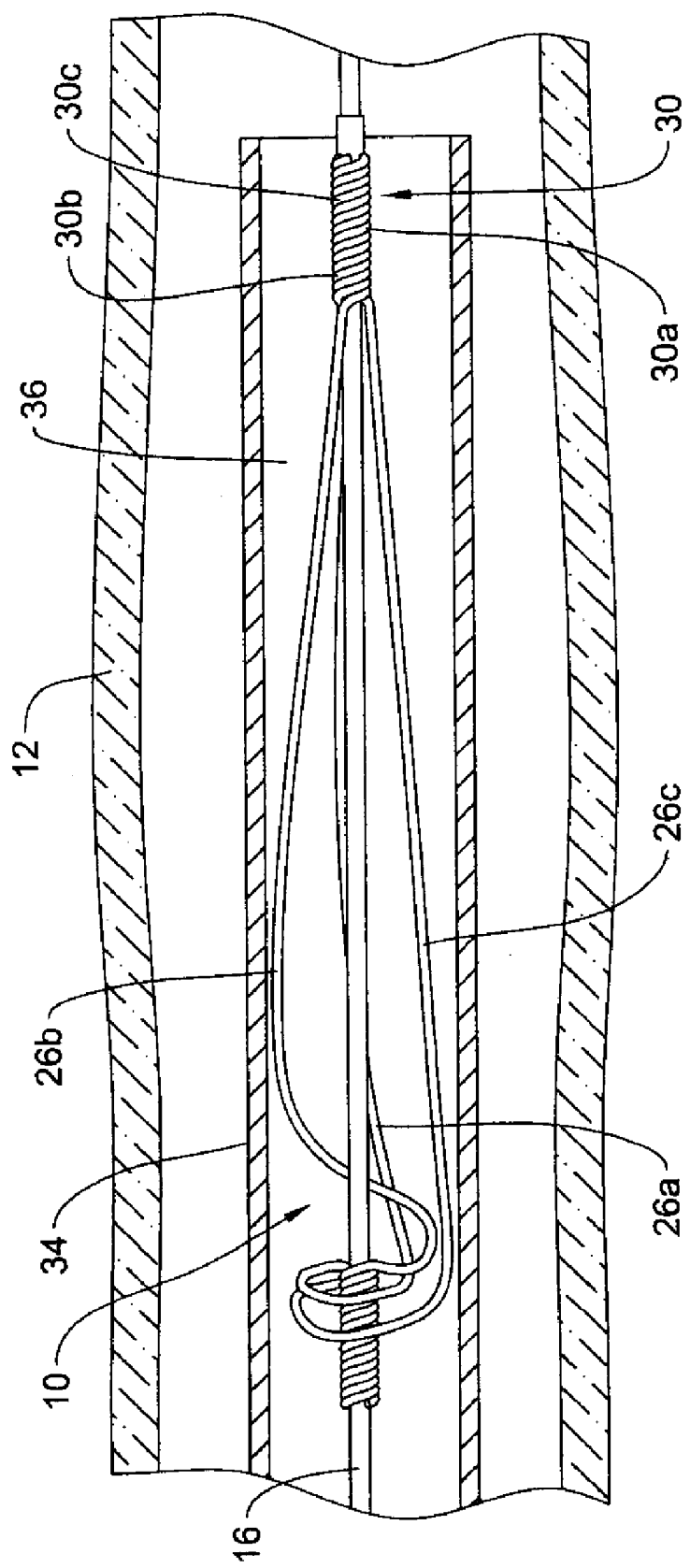
FIG. 3 is a partial cross-sectional side view of an example medical device collapsed within a delivery or retrieval sheath.

When device 10 and/or basket region 18 are in the collapsed configuration, it may be suited for being delivered via a suitable catheter or delivery sheath 34 as shown in FIG. 3. For example, it may be desirable to collapse basket region 18 and dispose it within a lumen 36 within sheath 34. It can be seen in FIG. 3 how distally moving distal end region 30 and/or distal ends 30a/b/c can help collapsed device 10 so that it may be easily be disposed in lumen 36. Additionally, it can be seen that as ends 30a/b/c are shifted, basket region 18 elongates. Accordingly, looped regions 26a/b/c also begin to straighten and elongate. Because the collapsing of device 10 and/or basket region 18 includes the longitudinal shifting of ends 30a/b/c and the elongation of basket region 18, outward radial forces may be reduced. This may allow device 10 to more easily be disposed in or otherwise advance through sheath 34. Moreover, the length of distally-extending regions 28a/b/c can be altered so that collapsing forces and radial forces can be further reduced. For example, elongating regions 28a/b/c may reduce the forces needed to collapse device 10 and reduce radial forces that might be exerted on the inside surface of sheath 34.

With basket region 18 collapsed within lumen 36, sheath 34 and device 10 can be advanced to the desired position (e.g., adjacent a clot) and sheath 34 can be proximally retracted so that device 10 emerges therefrom and can shift to the expanded configuration. Alternatively, device 10 can be delivered by first positioning sheath 34 at the desired location and then advancing device 10 through sheath 34. Regardless of how device 10 and basket 18 are moved into position, expanded basket 18 can be used to capture clot 20. In some embodiments, sheath 34 may also be used to aspirate clot 20 or other clots captured by device 10 by applying a vacuum to the sheath lumen 36.

Removal of device 10 may be accomplished in a number of different ways. For example, device 10 may be removed by simply retracting it proximally from the vasculature. This may include retracting basket 18 up to an introducer sheath disposed at the vascular access site. Once at the introducer sheath, the clot can be aspirated from basket 18 or removed together with basket 18. Alternatively, device 10 may be retracted up to or otherwise be disposed within a suitable retrieval sheath or catheter.

In some embodiments, catheter or sheath 34 may be a microcatheter. The dimensions and general configuration of the microcatheter can vary. For example, catheter 34 may have an inside lumen diameter of about 0.016 to about 0.022 inches, or more or less. These dimensions may allow sheath 34 to be suitably sized to access a number of different vascular targets while having a lumen sized sufficient to allow device 10 to advance through or otherwise be disposed therein. In addition or in the alternative, sheath 34 may include a distal housing section configured for having basket region 18 (or other portions of device 10) disposed therein. Of course, a number of other delivery devices may be used including essentially any suitable structure.

FIGS. 4 and 5 illustrate some of the other uses and features of device 10. For example, FIG. 4 illustrates that by configuring looped regions 26a/b/c so that mouth 22 is generally concentric with shaft 16, navigation through the vasculature can occur without spillage of captured clots 20 into the blood stream. This is because the concentric orientation of mouth 22 and shaft 16 allows mouth 22 to maintain apposition to the blood vessel wall. For example, when mouth 22 of device 10 is disposed in a side vessel 12a, the concentric orientation helps keep device 10 centered within vessel 12a. As device is retracted into the parent blood vessel 12, mouth 22 can quickly become centered within this vessel 12. Without the ability to center within a vessel or vessels, mouth 22 could end up being positioned so that a portion of it is pointed "downstream" so that clot 20 could flow out of basket region 18 and into the blood stream. Improved wall apposition may also be desirable by allowing basket region 18 to essentially filter the entire cross-sectional area of the vessel. Accordingly, it is less likely that clot 20 could by-pass basket region 18 and avoid capture.

FIG. 5 illustrates that mouth region 22 may also be adaptable to appose vessel of differing sizes. For example, device 10 may be navigating vessels 12 and 12a, and vessel 12a may have a cross-sectional area that is smaller than vessel 12. Accordingly, if mouth 22 was not configured to appose vessel of differing sizes, a portion of the bigger vessel 12 may be left unfiltered.

This adaptability may be accomplished in a number of ways. For example, struts 14a/b/c may be comprised of a shape-memory or super elastic material (including any of those described herein or any other suitable material) and set to a shape that is sized to appose a relatively large vessel (e.g., vessel 12). Other materials including linear elastic materials may also be used to have essentially the same effect. Regardless of what material is used, mouth 22 may be generally be amenable to being deformed to smaller sizes by constricting it within a smaller container (e.g., vessel 12a). However, mouth 22 can be configured so that constricting will not generally result in a plastic deformation in the material. Therefore, device 10 may be used in a small vessel, wherein mouth 22 is constrained somewhat to a smaller size, and still be able to expand to accommodate larger vessels. There may be a number of ways to account for the reduced mouth 22 size. For example, when mouth 22 is configured within a smaller vessel, adjacent looped regions 26a/b/c may overlap to a greater extent then when mouth 22 is disposed in a larger vessel. Because the shape-memory or linear material may be set or otherwise biased to be in a shape conforming to a generally larger vessel, when device 10 is then retracted to larger vessel 12, mouth 22 can then expand to appose the inside surface of that vessel 12. Thus, the use of overlapping looped regions 26a/b/c may help allow for mouth 22 to shift between a variety of different sizes while in use.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A medical device for removing clots from a blood vessel, comprising:
    an elongate shaft having a distal end;
    a plurality of struts, each strut having a first end coupled to the shaft, a loop region, a substantially linear region, and a second end attached to the shaft;
    wherein said loop regions overlap with one another and are disposed about the shaft; and
    wherein the second ends of the struts are the distal ends of the struts, and the distal ends are fixedly attached to the shaft.

2. The medical device of claim 1, wherein the distal end of the struts is fixedly attached to the shaft by winding the proximal ends about the shaft.

3. The medical device of claim 1, wherein the first end of the struts is the proximal end of the struts, and wherein the proximal end of the struts is slidably disposed along the shaft.

4. The medical device of claim 3, wherein the proximal end of the struts is attached to a tubular member disposed over the shaft.

5. The medical device of claim 1, wherein the loop regions are circumferentially disposed about the shaft.

6. The medical device of claim 1, wherein the struts are coupled with one another at one or more connection points in a folded sheet configuration.

7. The medical device of claim 1, wherein the struts comprise a shape-memory material.

8. The medical device of claim 7, wherein the shape-memory material is a nickel-titanium alloy.

9. The medical device of claim 1, wherein the loop regions are in a generally collapsed configuration.

10. The medical device of claim 1, wherein the loop regions are in a generally expanded configuration.

11. A medical device for removing emboli from a blood vessel, comprising:
   an elongate shaft having a distal end;
   a first strut having a first end coupled to the shaft, a first loop region, a first substantially linear region, and a second end attached to the shaft;
   a second strut having a first end coupled to the shaft, a second loop region, a second substantially linear region, and a second end attached to the shaft; and
   wherein the first and second loop regions overlap with one another and are disposed about the shaft; and
   wherein the second end of the first strut is the distal end of the first strut and the second end of the second strut is the distal end of the second strut; and the loop regions adaptably engage a wall of the blood vessel.

12. The medical device of claim 11, wherein the first end of the first strut is the proximal end of the first strut and the first end of the second strut is the proximal end of the second strut, when the proximal end of the first strut and the proximal end of the second strut are fixedly attached to the shaft.

13. The medical device of claim 11, wherein the second end of the first strut is the distal end of the first strut, wherein the distal end of the first strut is slidably disposed along the shaft.

14. The medical device of claim 13, wherein the distal ends of the struts are attached to a tubular member disposed over the shaft.

15. The medical device of claim 11, further comprising a third strut having a proximal end attached to the shaft, a third loop region, and a distal end coupled to the shaft.

16. The medical device of claim 15, wherein the third loop region overlaps with the first loop region, the second loop region, or both.

17. The medical device of claim 15, wherein the third loop region adaptably engages the wall of the blood vessel.

18. The medical device of claim 11, wherein the loop regions are in a generally collapsed configuration.

19. The medical device of claim 11, wherein the loop regions are in a generally expanded configuration.

20. The medical device of claim 19, wherein the loop regions engage the wall of a blood vessel when expandably configured.

* * * * *